(12) United States Patent
Petersen et al.

(10) Patent No.: US 8,790,250 B2
(45) Date of Patent: Jul. 29, 2014

(54) ENDOSCOPE BENDING SECTION CONTROL MECHANISM

(75) Inventors: Lasse Kjeld Gjoeske Petersen, Frederiksværk (DK); Louise Wagner Petersen, Copenhagen (DK)

(73) Assignee: AMBU A/S, Ballerup (DK)

( * ) Notice: Subject to any disclaimer, the term of this patent is extended or adjusted under 35 U.S.C. 154(b) by 193 days.

(21) Appl. No.: 13/133,704

(22) PCT Filed: Dec. 9, 2009

(86) PCT No.: PCT/EP2009/066727
§ 371 (c)(1),
(2), (4) Date: Aug. 22, 2011

(87) PCT Pub. No.: WO2010/066789
PCT Pub. Date: Jun. 17, 2010

(65) Prior Publication Data
US 2011/0295068 A1    Dec. 1, 2011

(30) Foreign Application Priority Data
Dec. 10, 2008 (DK) .................................. 2008 01758

(51) Int. Cl.
*A61B 1/00* (2006.01)
(52) U.S. Cl.
USPC ........................... 600/146; 600/131; 600/149
(58) Field of Classification Search
CPC ... A61B 1/0051; A61B 1/0052; A61B 1/0057
USPC ............ 600/146, 149, 131; 604/95.01–95.04, 604/528
See application file for complete search history.

(56) References Cited

U.S. PATENT DOCUMENTS 2,849,548 A * 8/1958 Young ........................... 200/6 A
4,926,172 A   5/1990 Gorsek (Continued)

FOREIGN PATENT DOCUMENTS

EP    0 357 274       3/1990
EP    1 046 406 A2   10/2000

(Continued)

OTHER PUBLICATIONS

International Search Report dated Mar. 19, 2010.

(Continued)

*Primary Examiner* — Anhtuan T Nguyen
*Assistant Examiner* — Jae Woo
(74) *Attorney, Agent, or Firm* — Finnegan, Henderson, Farabow, Garrett & Dunner LLP

(57) ABSTRACT

An endoscope (1) having a distal end being arranged to be inserted into a body cavity of a patient to be examined and a proximal end which is arranged to be held by a user of the endoscope. The endoscope further comprises a handle (2) arranged at the proximal end of the endoscope, an insertion portion (3) arranged at the distal end of the handle, a bending portion (4) arranged at the distal end of the insertion portion, and two control wires (40,41) arranged between the handle and the bending portion, said control wires being used to control the bending of the bending portion via control inputs made at the handle. The handle also comprises at least one lever member (21) being arranged to be pivotable about a pivot axis (22), a pulley element (42) located between the proximal end of the handle and the pivot axis of the lever member, and wherein said two control wires are attached to said at least one lever member, a first of said control wires (40) being arranged such that it travels from the at least one lever member (21) in the direction towards the bending portion (4) and the second of said two control wires (41) being arranged such that it travels from the at least one lever member (21) in the direction towards the pulley element (42), it then travels around the pulley element and it then travels towards the bending portion (4). In this way, a simple and effective control mechanism is provided.

12 Claims, 3 Drawing Sheets

(56) References Cited

U.S. PATENT DOCUMENTS

| | | | |
|---|---|---|---|
| 5,462,527 A * | 10/1995 | Stevens-Wright et al. | 604/528 |
| 5,541,622 A * | 7/1996 | Engle et al. | 345/161 |
| 5,626,553 A | 5/1997 | Frassica et al. | |
| 5,785,663 A * | 7/1998 | Sarvazyan | 600/587 |
| 5,889,507 A * | 3/1999 | Engle et al. | 345/161 |
| 6,236,034 B1 | 5/2001 | DeVolpi | |
| 6,440,062 B1 | 8/2002 | Ouchi | |
| 6,829,497 B2 * | 12/2004 | Mogul | 600/374 |
| 7,300,438 B2 * | 11/2007 | Falwell et al. | 606/41 |
| 7,524,301 B2 * | 4/2009 | Dubois et al. | 604/95.04 |
| 7,591,784 B2 * | 9/2009 | Butler | 600/146 |
| 7,794,392 B2 * | 9/2010 | Maruyama | 600/148 |
| 7,828,725 B2 * | 11/2010 | Maruyama | 600/148 |
| 2003/0092965 A1 * | 5/2003 | Konomura et al. | 600/146 |
| 2004/0267093 A1 | 12/2004 | Miyagi et al. | |
| 2005/0197536 A1 * | 9/2005 | Banik et al. | 600/179 |
| 2007/0255104 A1 | 11/2007 | Maruyama | |
| 2007/0282167 A1 * | 12/2007 | Barenboym et al. | 600/131 |
| 2009/0247994 A1 | 10/2009 | Bacher et al. | |

FOREIGN PATENT DOCUMENTS

| | | |
|---|---|---|
| EP | 2 106 751 A1 | 10/2009 |
| JP | 42-10451 | 6/1942 |
| JP | S49-91184 | 11/1947 |
| JP | H06-66619 | 3/1994 |
| JP | 11-216103 | 8/1999 |
| JP | 2004-321612 | 11/2004 |
| WO | WO 2007/092636 A2 | 8/2007 |

OTHER PUBLICATIONS

International Preliminary Report on Patentability dated Mar. 4, 2011.

English Translation of Office Action in Japanese application No. 2011-540074, dated Aug. 13, 2013 (3 pages).

English Translation of Search Report in Chinese application No. 200980153972.1, dated Jul. 15, 2013 (2 pages).

English Translation of Office Action in Chinese application No. 200980153972.1 (8 pages).

* cited by examiner

ENDOSCOPE BENDING SECTION CONTROL MECHANISM

The current invention relates to an endoscope having a distal end being arranged to be inserted into a body cavity of a patient to be examined and a proximal end which is arranged to be held by a user of the endoscope. The endoscope further comprises a handle arranged at the proximal end of the endoscope, an insertion portion arranged at the distal end of the handle, a bending portion arranged at the distal end of the insertion portion, and two control wires arranged between the handle and the bending portion, said control wires being used to control the bending of the bending portion via control inputs made at the handle.

The type of endoscope described in the opening paragraph is well known to the person skilled in the art and comes in many different shapes and sizes. The opening paragraph should therefore be construed as broadly as possible.

DESCRIPTION OF RELATED ART

An example of such an endoscope is disclosed in U.S. Pat. No. 5,976,075. In this case a very simple mechanism is provided to control the bending of the bending portion of the endoscope. Another example of a simple mechanism is disclosed in EP 1,804,639. Another example is WO 94/10897. This example shows a more complex arrangement whereby the bending portion can be better controlled with more degrees of freedom. Many other examples can be found in the patent literature.

We note that the current invention is, as mentioned above, related to endoscopes. However, the main focus of the application is on the handle portion and the mechanism within the handle portion for controlling the bending of the bending portion of the endoscope, i.e. the mechanism for controlling the motion of the two control wires. The remaining structure of the endoscope is not so important for the current invention and as such, the remaining structure will not be discussed in great detail in the current specification. The person skilled in the art should however be able to see how the current handle/control mechanism can be integrated into endoscopes of different forms without any great difficulties.

We note that in the current application, the example endoscope shown is an endoscope used to help in establishing artificial respiration for patients. At the start of the procedure an endotracheal tube is placed over the flexible insertion portion of the endoscope. Once the endotracheal tube is place on the insertion portion, the flexible insertion portion is inserted into the airway of a patient. The vision system in the tip of the endoscope allows the endoscope to be guided into place without danger for the patient. Once the endoscope is in place, the endotracheal tube can be pushed down along the insertion portion of the endoscope. Once the endotracheal tube is in place, the endoscope can be withdrawn leaving the endotracheal tube in place in the airway of the patient. While this is the only concrete embodiment disclosed in this specification, it should be understood that the teachings of the current specification can apply to many other types of endoscopes as well. Two non limiting examples are an endoscope used during surgery to view the surgical procedure and an endoscope used in industry to inspect machinery or other structures.

Furthermore the endoscopes can have a different form than the one discussed in this application. For example, the endoscope shown in the figures comprises a flexible insertion portion. However, a handle/control mechanism according to the current invention could also be used with an endoscope having a stiff insertion portion and a bending portion arranged at the end of the stiff insertion portion.

SUMMARY OF THE INVENTION

It is a first aspect of the current invention to provide an endoscope which is better than the prior art endoscopes. In particular, an aspect of the current invention is to provide an endoscope handle/control mechanism having a reduced cost and complexity.

This aspect is in part provided by an endoscope as specified in the opening paragraph and further comprising at least one lever member arranged to be pivotable about a pivot axis, a pulley element located between the proximal end of the handle and the pivot axis of the lever member, and wherein the two control wires are attached to the at least one lever member, a first of said two control wires being arranged such that it travels from the at least one lever member in the direction towards the bending portion and the second of said two control wires being arranged such that it travels from the at least one lever member in the direction towards the pulley element, it then travels around the pulley element and then forwards towards the bending portion. In this way, a simple and effective control mechanism can be achieved.

It should be mentioned that according to the current specification, the term "pulley element" should be interpreted as any element which allows the direction of a flexible element, such as a string or control wire, to change direction. This could be a pulley with a rotatable wheel as a support surface for the flexible element, or it could be a fixed surface around which the flexible element is arranged. It could also be a wire sheath which changes directions, for example a thin metal or stiff plastic tube bent into a U shape, the wire being arranged inside the tube. This could for example be a Bowden cable.

The term "lever member" according to this specification should be understood as any element which allows a leverage force to be applied to an element. Two non-limiting examples are a stiff rod pivotable about a pivot axis and a cylinder pivotable about a pivot axis and around which a flexible member is arranged. The person skilled in the art will be able to provide equivalent structures. Furthermore, more than one lever members could be connected together and each control wire could be connected to a different lever member.

In one embodiment, the first and second control wires could be attached to the at least one lever member on the same side of a plane passing through the pivot axis.

In a preferred embodiment, the pivot axis of the at least one lever member could be arranged perpendicular to the longitudinal axis of the insertion portion of the endoscope. In this way, the motion of the wires will be essentially aligned with the axis of the insert portion. It should be noted that since the insertion portion is flexible, the longitudinal axis of the insertion portion can change. However for the understanding of this paragraph, the longitudinal axis of the most proximal part of the insertion portion should be used.

In order to ensure that the control wires move in relatively the same direction and in relatively the same amount, the angle formed between a first vector defined by the attachment point of the first control wire to the at least one lever member and the pivot axis of the at least one lever member and a second vector defined by the attachment point of the second control wire to the at least one lever member and the pivot axis of the at least one lever member could be less than 120°. The smaller the angle, the more the two points will follow the same path. In a preferred embodiment the angle could be less than 45 degrees. In another preferred embodiment the angle is essentially zero. It should be noted that the angle is measured by projecting the vectors onto a plane which is perpendicular to the pivot axis.

Furthermore, the attachment points of the control wires could be arranged such that the distance from the attachment point of the first control wire on the at least one lever member to the proximal end of the handle and the distance from the attachment point of the second control wire on the at least one lever member to the proximal end of the handle could be essentially the same.

In order to control the lever member, the control handle could comprise a housing which comprises an opening through which a control element protrudes. The control element could be connected to the at least one lever member. The control element for the sake of this specification should be understood as an element whereby the user of the endoscope can control the motion of the at least one lever member. This could for example be a slideable button or a turnable knob. The person skilled in the art will be able to provide additional possibilities.

In one embodiment, the opening in the housing could be arranged as a slot. In this case, the at least one lever member could comprise a shield member arranged on the inner side of the housing of the handle which covers said slot from the inside of the housing of the handle. The shield member could furthermore be displaceable together with the at least one lever member. In this way a nice finish is achieved without any open holes in the housing. In addition, the shield member will close the housing, so foreign matter can be prevented from getting inside the housing. The shield member could also be provided with seals in order to completely seal the opening.

In another embodiment, the handle could comprise a spring member connected to the at least one lever member and arranged to return the at least one lever member to a neutral position. By neutral position it should be understood as a position where the bending portion is in a straight position, as shown by the solid lines in FIG. 1. The lever member will typically be arranged to be able to be displaced to either side of this neutral position.

In a preferred embodiment, the handle could further comprise a second spring member and in that the first and second spring members are arranged one on either side of a plane which is arranged perpendicular to the pivot axis of the at least one lever member. In this way, the two springs will be able to provide a balanced torque on the lever member.

The spring member could advantageously be formed as a leaf spring comprising at least one leaf.

In a particularly simple embodiment, the spring member could be arranged to pass through the pivot axis of the at least one lever member.

The at least one lever member could furthermore be at least partially supported in the handle via an axle arranged co-axially with the pivot axis of the at least one lever member and supported in a support member arranged in the handle. The axle could be directly connected with the spring member.

In a specific embodiment, the handle could comprise two leaf springs, each leaf spring comprising at least one leaf and being arranged on either side of a plane which is arranged perpendicular to the pivot axis of the a least one lever member, said leaf springs being arranged to pass through the pivot axis of the at least one lever member and said at least one lever member being connected to the leaf springs in the middle of the leaf springs, the ends of the leaf springs being fixedly supported within the handle.

The ends of the leaf springs could furthermore be sandwiched between a top cover portion of a housing of the handle and a bottom cover portion of the housing of the handle. This will provide a simple assembly procedure.

In a preferred embodiment, the control wires could be a part of two Bowden cable assemblies and the ends of the sheaths of the Bowden cable assemblies could be adjustably arranged within the handle of the endoscope. In this way, the control wires can be arranged more flexibly in the handle and the tension in the control wires can be easily adjusted.

It should be emphasized that the term "comprises/comprising/comprised of" when used in this specification is taken to specify the presence of stated features, integers, steps or components but does not preclude the presence or addition of one or more other features, integers, steps, components or groups thereof. For example in the introductory paragraph it is mentioned that the endoscope comprises two control wires. However, this should also include any additional number of control wires.

BRIEF DESCRIPTION OF THE DRAWINGS

In the following, the invention will be described in greater detail with reference to embodiments shown by the enclosed figures. It should be emphasized that the embodiments shown are used for example purposes only and should not be used to limit the scope of the invention.

DETAILED DESCRIPTION OF THE EMBODIMENTS

Figure 1:
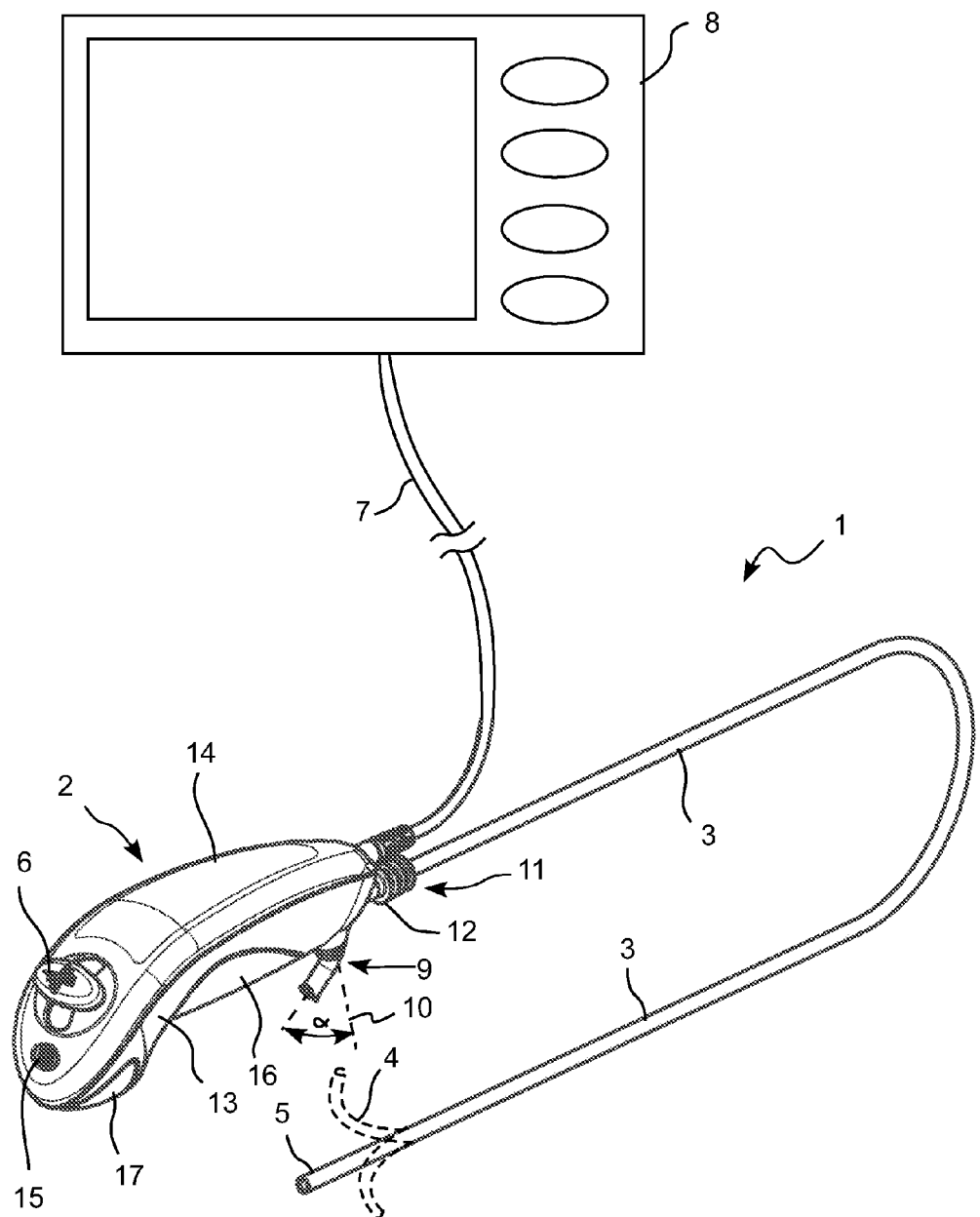
FIG. 1 shows a complete perspective view of an endoscope according to the invention together with a schematic representation of its supporting hardware.

The endoscope 1 shown in FIG. 1 comprises a control handle 2, a flexible insertion portion 3, a bending portion 4 and a rigid tip portion 5. The control handle comprises a control member 6 arranged on the outside of the housing of the handle. The control member in the current embodiment is in the form of a joystick 6 which is connected to the bending portion 4 via Bowden cables (not shown in FIG. 1) arranged partly within the control handle, the flexible insertion portion and the bending portion. When the joystick is displaced, the bending portion bends as shown by the dashed lines in FIG. 1.

The control handle further comprises an electrical cable 7 which is used to connect the endoscope to a control module 8. In the current embodiment, the control module comprises a power source and a video monitor. The control handle also comprises an injection port 9 which is in communication with an opening (not shown) at the distal end of the rigid tip portion of the endoscope via a flexible tube (or working channel) arranged partly within the control handle, the flexible insertion portion and the bending portion. The injection port 9 can be used to inject fluids into the endoscope which will be sprayed out at the opening at the tip of the endoscope. This could for example be a local anaesthetic or the like.

The flexible insertion portion 3 is arranged as a hollow tube which is flexible and bendable about directions perpendicular to the longitudinal axis of the insertion portion. However, the flexible insertion portion is stiff in the torsional direction and in the longitudinal direction. In this way, rotation of the control handle is transferred directly to the tip and allows the user of the endoscope to control the rotational position of the tip of the endoscope by twisting the control handle. A camera and a light source (not shown) are arranged in the rigid tip portion 5 of the endoscope. The electrical signals from the camera and the power to the camera and the light source art are transferred via wires (not shown) partly arranged within the control handle, the flexible insertion portion and the bending portion of the endoscope. The electrical signals are transferred from the rigid tip to the control handle where after they are further transferred to the control module for displaying on the video monitor.

It should be noted that endoscopes comprising the above mentioned features are very well known to the person skilled in the art and further details will not be required by the person skilled in the art to understand and implement the current invention. The main invention disclosed in the current application is directed to the mechanism in the control handle used to control the bending of the bending portion. This specification will therefore focus on this invention.

FIG. 1 does however show two features which are not directly related to the main invention and which are different from prior art endoscopes. These features are described in the context of the current invention, but it should be clear to the person skilled in the art that these two features could become the subject matter of two separate divisional applications.

The first feature relates to the injection port 9. In the current embodiment, the injection port 9 is formed as a swivel which is able to rotate about a rotation axis 10. In the current embodiment, the rotation axis is arranged on a plane which is parallel to the plane of symmetry of the control handle. However the rotation axis could also be arranged along a different plane in another embodiment. Furthermore, the connection part of the injection port extends at an angle α of between 10 and 90 degrees to the rotation axis. By providing the connection part of the injection port at an angle to the rotation axis, it is possible to rotate the connection part such that it will point to either side of the handle. In this way it is easier for an assistant to assist the user of the endoscope when something needs to be injected into the injection port. In prior art type endoscopes, the injection ports are typically arranged to protrude from the control handle at a fixed orientation. In contrast, the injection port of the current invention can be swivelled towards the direction of the assistant to the user. The details of the swivel can be better seen in FIG. 4.

Figure 5:
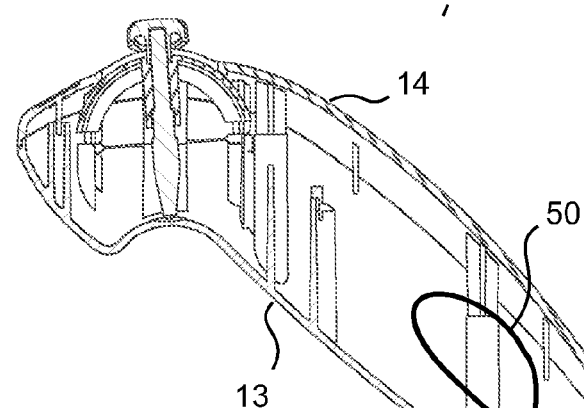
FIG. 5 shows the same cross section as FIG. 4, however without the control wires, but showing the injection tube and the electrical signal wire.

As can be seen in FIG. 5, the flexible tube or working channel 50 which is connected to the injection port is arranged as a loop within the handle. In this way, the portion of the tube connected to the injection port is able to be fixed to the injection port and the loop absorbs the rotation of the tube due to the rotation of the injection port. In order not to stress the tube too much, the injection port can be arranged such that it can only rotate a certain amount in either direction for example approximately 90° in either direction. An embodiment where the motion is limited to approximately 60° in either direction is also imagined.

The second feature relates to a fastening device 11 for fastening the endotracheal tube to the end of the handle of the endoscope while inserting the endoscope into the airway of the patient. The fastening device is arranged at the proximal end of the insertion portion (and/or at the distal end of the handle. The fastening device comprises at least one flexible ring 12 arranged around the outer diameter of the insertion portion. In this particular embodiment the fastening device comprises four flexible rings 12, but any other number of rings is possible. The rings 12 are formed from a suitable flexible material, for example rubber. The rings are co-axial with the axis of the insertion portion at the proximal end of the insertion portion.

The rings have an outer diameter which is slightly larger than the inner diameter of a standardized connector at the end of an endotracheal tube. In this way, the endotracheal tube (not shown) which is placed over the insertion portion before the endoscope is inserted into the airway of a patient, can be pushed towards the handle whereby the connector of the endotracheal tube is pushed towards the fastening device whereby the rings of the fastening device are pressed into the opening in the connector due to their flexibility. The rings then hold on to the endotracheal tube via friction between the rings and the connector on the endotracheal tube. When the endotracheal tube is to be released, the user can apply a light force to the endotracheal tube to disengage the tube from the rings.

Endotracheal tubes come in many different sizes typically between 2 and 10.5 mm in internal diameter. In order to use the different sized endotracheal tubes with the same equipment, standard connectors have been developed which are mounted at the end of the endotracheal tubes. The outer surface of the connector is a standardized cone shape with a nominal diameter of 15 mm. The inner diameter of the connector is not standardized, but is in most of these connectors around 11 mm. Since the inner diameter of the connector is not standardized, there will be slight variations in the inner diameter of the connectors of different manufacturers. However with the arrangement of the fastening device as disclosed herein, the flexible nature of the rings of the fastening device will flex and work with a large number of different sizes.

It should also be mentioned that the rings could be arranged in many different manners. For example, the rings in a certain embodiment could be arranged to taper in the direction towards the control handle. In this way, the wedging effect of the fastening device could be increased. In another embodiment, the rings of the fastening device could be arranged to have a non-circular periphery. For example, the rings could be arranged in a star like shape. In this way, the points of the star would hold onto the inner surface of the endotracheal tube. Using a star like shape would allow the rings to accept a larger variation of connector sizes without making the rings too soft.

The control handle 2 further comprises a housing which comprises a main housing part 13 and a cover part 14. An on/off push button 15 is arranged on the cover part of the housing. The main part of the housing and the cover part are formed from a plastics material in an injection moulding process in the current embodiment. The main part of the housing furthermore comprises two areas 16,17 which are covered in a softer and more gripable material when compared to the rest of the housing and cover part. This material could for example be a rubber like material. This type of covering is known from power tools such as power drills, etc. and provides the user with a better and more comfortable grip on the handle. The same type of covering is also applied to the joystick 6.

Figures 2, 3:
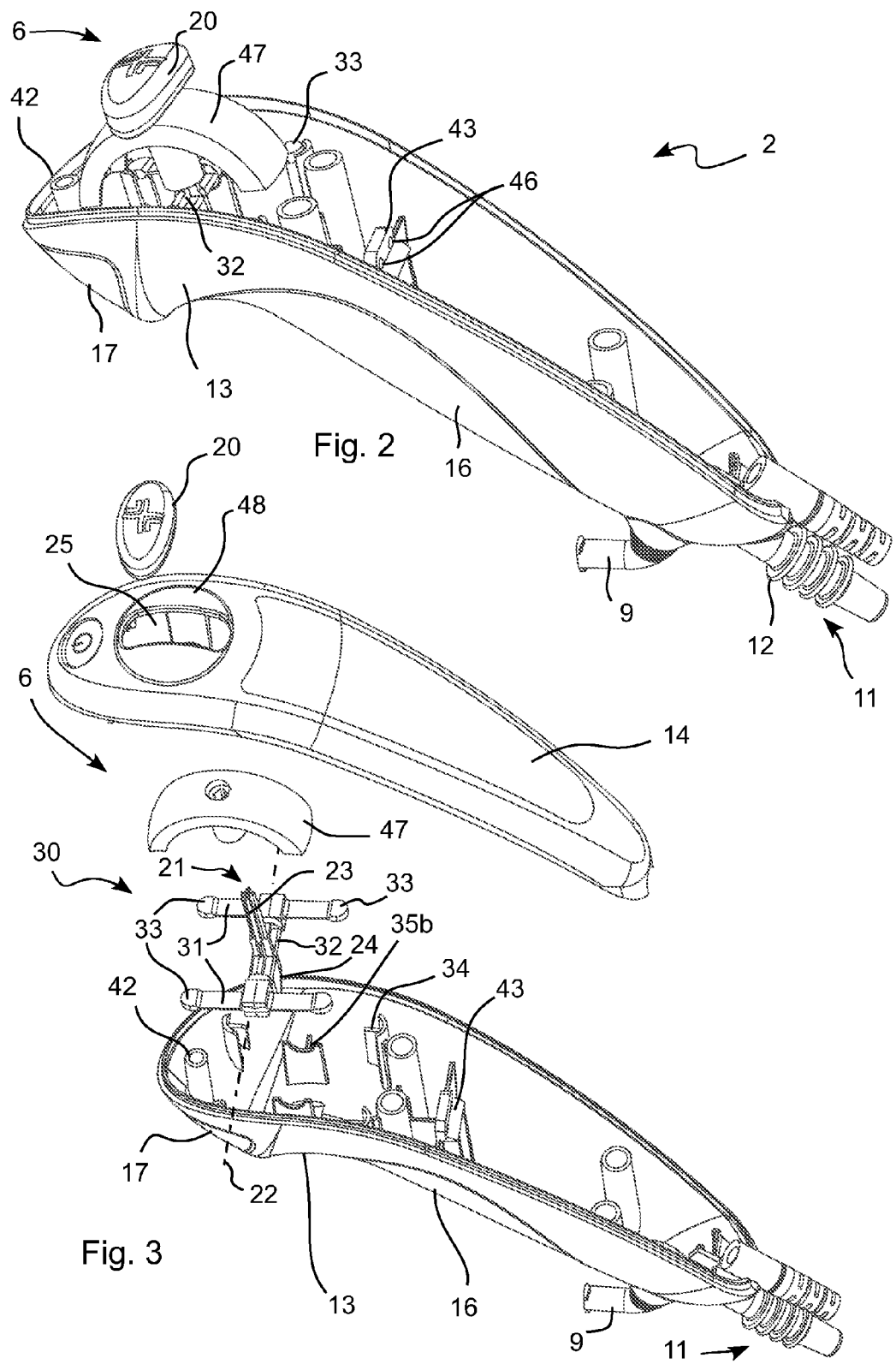
FIG. 2 shows a more detailed perspective view of the handle of the endoscope of FIG. 1 with a top cover portion of the housing removed.
FIG. 3 shows a perspective exploded view of the handle of the endoscope of FIG. 1.
Figure 4:
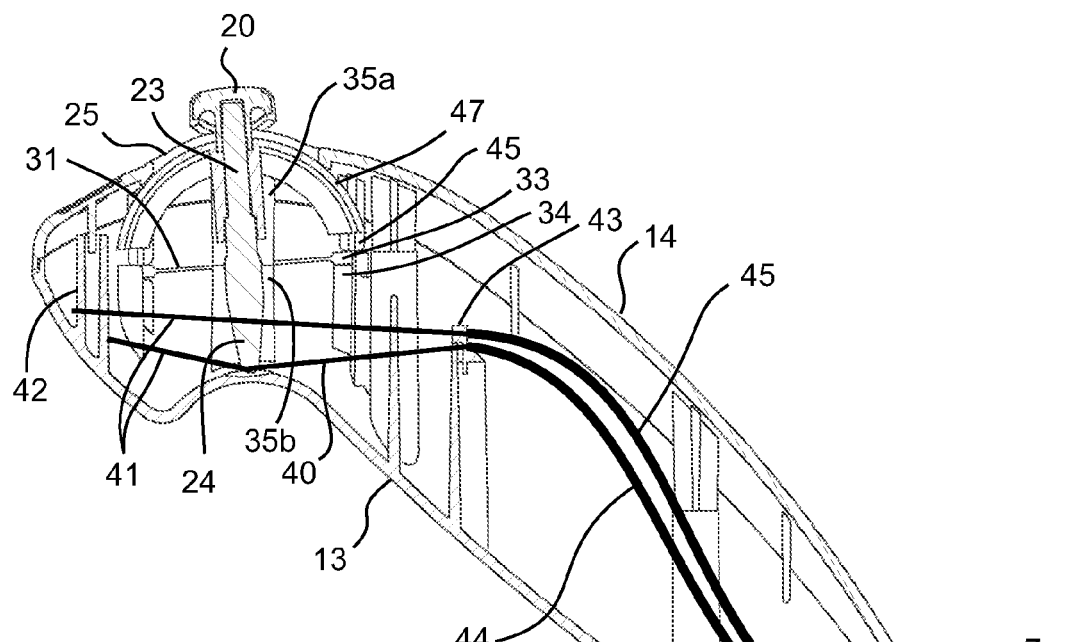
FIG. 4 shows a cross section of the handle of the endoscope of FIG. 1 showing the path of the control wires.

FIGS. 2-4 show the handle in more details so that the internal mechanical details of the control mechanism can be seen. It should be noted that the control wires are not shown in FIGS. 2 and 3, but are shown in the cross section of the handle shown in FIG. 4.

The handle 2 comprises a joystick mechanism 6 which comprises a displaceable button 20 which is arranged on the outer side of the housing of the control handle. The user controls the joystick mechanism via this displaceable button. In the current embodiment, the button is arranged to be able to move along a curved path arranged on a plane. In the current embodiment, said plane is arranged along the plane of symmetry of the handle. The button is connected to a lever member 21. The lever member is arranged to be pivotable about a pivot axis 22. The path of the motion of the button is therefore determined by the dimensions of the lever member and the location of the pivot axis 22. The lever member has a first portion 23 arranged on a first side of a plane which passes through the pivot axis and a second portion 24 arranged on the other side of said plane. The first portion of the lever member is arranged to protrude out of the housing via a slot 25 (see FIGS. 3 and 4) in the top cover part of the housing. The button 20 is connected to the first portion of the lever member.

The lever member 21 is supported within the housing of the handle via a suspension mechanism 30. The suspension mechanism is comprised of two leaf springs 31. In the current embodiment, each leaf spring comprises a single leaf. In other embodiments, the leaf springs could comprise additional leaves. The two leaf springs are arranged an equal distance on either side of a plane which is parallel to the plane of symmetry of the handle. The two leaf springs are connected to the lever member via an axle 32 which is co-axial with the pivot axis 22 of the lever member. The leaf springs are furthermore arranged such that they pass through the pivot axis of the lever member. The ends 33 of the leaf springs are mounted/supported in mounts 34 firmly connected to the housing of the control handle. The mounts prevent the ends of the leaf springs from moving up or down, but do not prevent sideways displacement (according to the orientation as shown in FIG. 4).

The axle 32 is supported within the housing via supports 35 in the handle. The supports 35 in the handle are formed as two complementary elements, an upper support element 35a connected to the cover part 14 of the housing of the handle and a lower support element 35b connected to the main portion 13 of the housing of the handle. The two complementary elements 35a,35b are formed with two semicircular openings which when put together form a complete circle. During assembly the axle can be laid in the lower support element and then held in place with the upper support element when the cover part is mounted on the main portion of the housing. In this way, any motion of the button causes the lever member to pivot about the pivot axis. The leaf springs force the lever member to return to a centred/netural position when the user releases the button.

As can be seen from FIG. 4, the two control wires 40, 41 are connected to the second portion of the lever member. In other words, the control wires are connected to the lever member on the opposite side of a plane passing through the pivot axis as the button 20. The first control wire 40 is connected to the end of the lever member and then runs forwards towards the distal end of the handle and ends up at the distal end of the bending portion. Note the direction "forwards" should be understood as a direction from the proximal end of the endoscope towards the distal end. The term "backwards" should be understood as a direction from the distal end of the endoscope towards the proximal end. The second control wire 41 is connected to the end of the lever member at essentially the same position as the first control wire. By essentially the same, is meant close together such that the motion of the two connection points is roughly the same. From its attachment to the lever member the second control wire runs backwards and then passes around a pillar 42 arranged in the housing. The pillar 42 acts as a sort of pulley element allowing the control wire to change direction and run forwards in the housing. As with the first control wire, the second control wire then runs to the distal end of the bending portion.

When the button is displaced in a direction towards the distal end of the handle, the lever member will rotate in a clockwise direction (according to the orientation of the handle as shown in FIG. 4) and tension will be applied to the first control wire 40 and the second control wire 41 will be slackened. When the button is displaced in a direction towards the proximal end of the handle, the lever member will rotate in a counter clockwise direction and tension will be applied to the second control wire 41 and the first control wire will be slackened. In the second case, the end of the second control wire 41 which is attached to the lever member will be pulled forwards, ie towards the distal end of the handle. The second control wire will then transfer this pull via the pillar 42 into a pull backwards on the portion of the second control wire which is arranged between the pillar and the distal end of the bending portion.

The two control wires 40,41 are arranged to pass through holes 46 in a support pillar 43 firmly fixed in the housing in order to control the paths of the control wires. In the current embodiment, in order to better control the travel of the control wires, the control wires are formed as parts of Bowden Cables. A Bowden cable is well known from other endoscope systems and more commonly from bicycle cable arrangements. A Bowden cable is comprised of an active cable part arranged inside a sheath. The sheath is arranged to be relatively incompressible in the longitudinal direction. In this way the path of the control wires can be controlled very well and allow the pull to change directions. In addition, the sheaths protect the cables from kinking and reduce the friction against movement of the control cables.

In the current embodiment, the sheath 44 of the first control cable 40 and the sheath 45 of the second control cable are both attached at one end to a support pillar 43 in the handle and are both attached at the other end to the proximal end of the bending portion. The support pillar 43 is furthermore arranged such that the proximal ends of the sheaths point at the lever member, and essentially in the direction towards the point where the control wires are attached to the lever member. In this way, each control wire, coming from the lever member, enters its respective sheath at the best possible angle to reduce friction. The sheaths then proceed from the support pillar in a smooth arc to the entrance of the insertion portion. The sheaths continue all the way to the proximal end of the bending portion. The support pillar 43 is furthermore formed to allow the end positions of the sheaths to be independently adjusted. By adjusting the end position of the sheaths, the same effect is achieved as if the sheaths were lengthened. In this way the tension on the control cables 40,41 can be adjusted. This could for example be made by providing two holes 46 in the support pillar with internal threads and arranging a hollow screw (not shown) in each hole. The hollow screw would be arranged to allow the control wire to pass through the hollow portion of the screw but prevent the sheath from passing the screw. By adjusting the screw, the position of the end of the sheath could be adjusted. This sort of adjusting mechanism is known from bicycle cables systems, for example brake or shifter cables.

It should be noted that in FIG. 4, the paths of the control wires 40,41 and the wire sheaths 44,45 are shown schematically in order to show the paths of the two wires separately. In a real device, the control wires would be arranged at the same height in the holes 46 in the support pillar 43 and as such would follow two paths which are closer to each other than shown in the figure.

As can be seen from FIG. 4, the joystick mechanism is also provided with a shielding portion 47. The shielding portion is fixed to the lever member and is formed from a semi circular element which is slightly wider than the slot 25 in the cover of the housing of the handle. The centre point of the semi circular element of the shielding portion is arranged co-axial with the pivot axis of the lever member. The semi circular portion is also arranged such that it covers the slot in both the position in which the joystick is pushed fully forward or pushed fully backwards. This means that the shielding portion is both longer and wider than the slot in the housing. As can be seen from FIG. 4, the shielding portion is quite large and would conflict with the control wires, if the control wires were mounted to the first portion of the lever member. Furthermore, it can be seen from FIGS. 3 and 4 that the area 48 of the top cover part 14 of the housing of the handle around the slot is also formed to fit with the curvature of the shielding portion 47.

The current embodiment of the handle mechanism is assembled by first forming the lever member 21 and the axle 32 as a single integrated plastic injection moulded component. The leaf springs 31,32 are separate plastic injection moulded components and are assembled together with the ends of the axle. According to the figures, the leaf springs are formed with an attachment portion in the middle of the leaf springs which fits into a corresponding recess in the ends of the axle. The ends 33 of the leaf springs are the placed in the mounts 34 in the bottom part of the housing and the axle 32 is arranged in the lower support elements 35*b*. The control wires are attached to the second portion 23 of the lever portion and the control wires arranged in the housing. The shielding portion 44 is then slid over the first portion of the lever member where after the top part 14 of the housing of the handle is mounted on the bottom part. The ends 33 of the leaf springs are then held in position in the housing by being sandwiched between protrusions 45 of the top cover part 14 and the mounts 34 of the bottom 13 of the housing of the handle and the axle is held in place by the support mounts 35*a*,35*b*. This can be seen in FIG. 4. Once the cover is in place, the button 20 is mounted to the first portion of the lever portion. The different components can be glued together to achieve a more firm assembly.

In order not to complicate FIG. 4 unnecessarily, the flexible tube or "working channel" connecting the injection port 9 and the opening (not shown) at the distal end of the endoscope and the wire connecting the camera electronics in the rigid tip of the endoscope and the control module have not been shown in FIG. 4. FIG. 5 however, shows how the tube 50 and the wire 51 are arranged to avoid the risk of kinking. It should furthermore be noted that not all the components of the endoscope have been shown in the figures. This is to avoid complicating the figures unnecessarily. For example, a printed circuit board comprising control electronics for the endoscope could be arranged within the handle as well.

It is to be noted that the figures and the above description have shown the example embodiments in a simple and schematic manner. The internal electronic and mechanical details have not been shown since the person skilled in the art should be familiar with these details and they would just unnecessarily complicate this description.

It should also be noted that the above described embodiments only disclose a small number of different embodiments which should be covered within the scope of the claims. For example in the embodiments shown, the control wires have been directly connected to the lever member. However, the person skilled in the art will understand that the control wires do not have to be directly attached to the lever member, but could be connected via a connection element, for example a stiff rod or the like. As such, the scope of the claims should not be limited by the embodiments unnecessarily.

It should also be noted that the disclosure of the arrangement of the leaf springs has only been described with regards to the embodiment shown in the figures, ie an embodiment where the control wires attached to the lever member go in opposite directions away from the lever member. However, the arrangement of the leaf springs as described in this specification could also be used together with other types of lever members. For example, consider the case of two cylindrical lever members arranged one on either side the shielding element shown in FIGS. 2 and 3 and co-axial with the axle. A first control wire is attached to a first cylindrical lever member and the second control wire is attached to the second cylindrical lever member. The second portion 24 of the lever member as shown in FIG. 2-4 could in this case be neglected. The pulley element 42 could also be neglected. As will be clear to the person skilled in the art, the leaf spring arrangement could therefore be used with embodiments which do not fall into the scope of the claims as currently filed. This is therefore a separate invention which might be claimed in a divisional application directed to this feature.

It can also be mentioned that the current embodiments have disclosed embodiments where the control input member has been a displaceable button. However other options as control input members should also be included, for example a turnable knob.

The invention claimed is:

1. An endoscope having a distal end being arranged to be inserted into a body cavity of a patient to be examined and a proximal end which is arranged to be held by a user of the endoscope, said endoscope comprising:
    a. a handle arranged at the proximal end of the endoscope,
    b. an insertion portion arranged at the distal end of the handle,
    c. a bending portion arranged at the distal end of the insertion portion, and
    d. two control wires arranged between the handle and the bending portion, said control wires being used to control the bending of the bending portion via control inputs made at the handle, wherein
    the handle comprises
    at least one lever member supported within a housing of the handle via an axle and arranged to be pivotable about a pivot axis arranged coaxially with said axle,
    a pulley element located between the proximal end of the handle and the pivot axis of the lever member, wherein said two control wires are attached to said at least one lever member, a first of said control wires being arranged such that the first control wire travels from the at least one lever member in a direction towards the bending portion and the second of said two control wires being arranged such that the second control wire travels from the at least one lever member in a direction towards the pulley element, the second control wire then travels around the pulley element and then travels towards the bending portion, wherein the handle comprises a first spring member connected to the at least one lever member and arranged to return the at least one lever member to a neutral position, wherein the first spring member is in the form of a leaf spring comprising at least one leaf and that the leaf spring is formed with an attachment portion in the middle of the leaf spring, which fits into a corresponding recess in the ends of the axle, the ends of the leaf spring being fixedly supported within the handle, said ends of the leaf spring are sandwiched between a top cover portion of the housing of the handle and a bottom cover portion of the housing of the handle.

2. An endoscope according to claim 1, wherein the first and second control wires are attached to the at least one lever member on the same side of a plane passing through the pivot axis.

3. An endoscope according to claim 1, wherein the pivot axis of the at least one lever member is arranged perpendicular to a longitudinal axis of the insertion portion of the endoscope.

4. An endoscope according to claim 1, wherein an angle formed between a first vector defined by an attachment point of the first control wire to the at least one lever member and the pivot axis of the at least one lever member and a second vector defined by an attachment point of the second control wire to the at least one lever member and the pivot axis of the at least one lever member is less than 120°, said angle being measured by projecting the vectors onto a plane which is perpendicular to the pivot axis.

5. An endoscope according to claim 1, wherein a distance from the attachment point of the first control wire on the at least one lever member to the proximal end of the handle and a distance from the attachment point of the second control wire on the at least one lever member to the proximal end of the handle are essentially the same.

6. An endoscope according to claim 1, wherein the handle of the housing comprises an opening through which a control element and/or said at least one lever member protrudes, said control element being connected to the at least one lever member.

7. An endoscope-according to claim 6, wherein said opening is a slot and the at least one lever member comprises a shield member arranged on the inner side of the housing of the handle which covers said slot from an inside of the housing of the handle, said shield member being displaceable together with the at least one lever member.

8. An endoscope according to claim 1, wherein the first spring member is arranged to pass through the pivot axis of the at least one lever member.

9. An endoscope according to claim 8, wherein the at least one lever member is at least partially supported in the handle via the axle arranged co-axial with the pivot axis of the at least one lever member and partially supported in a support member arranged in the handle and the axle is connected with the first spring member.

10. An endoscope according to claim 1, wherein the handle comprises a second leaf spring, each leaf spring comprising at least one leaf and being arranged on either side of a plane which is arranged perpendicular to the pivot of the at least one lever member, said leaf springs being arranged to pass through the pivot axis of the at least one lever member and said at least one lever member being connected to the leaf springs in a middle of the leaf springs, ends of the leaf springs being supported within the handle.

11. An endoscope according to claim 1, wherein the two control wires are a part of two Bowden cable assemblies and ends of the sheaths of the Bowden cable assemblies are adjustably arranged within the handle of the endoscope.

12. An endoscope according to claim 11, wherein the handle further comprises a second spring member and the first and second spring members are arranged one on either side of a plane which is arranged perpendicular to the pivot axis of the at least one lever member.

* * * * *